US010595734B2

(12) United States Patent
Thakur et al.

(10) Patent No.: US 10,595,734 B2
(45) Date of Patent: Mar. 24, 2020

(54) DIAGNOSTIC AND OPTIMIZATION USING EXERCISE RECOVERY DATA

(71) Applicant: Cardiac Pacemakers, Inc., St. Paul, MN (US)

(72) Inventors: Pramodsingh Hirasingh Thakur, Woodbury, MN (US); Qi An, Blaine, MN (US); Barun Maskara, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 334 days.

(21) Appl. No.: 15/132,705

(22) Filed: Apr. 19, 2016

(65) Prior Publication Data

US 2016/0228012 A1     Aug. 11, 2016

Related U.S. Application Data

(63) Continuation of application No. 14/195,626, filed on Mar. 3, 2014, now Pat. No. 9,345,410.

(60) Provisional application No. 61/798,452, filed on Mar. 15, 2013.

(51) Int. Cl.
| | | |
|---|---|---|
| *A61B 5/024* | (2006.01) | |
| *A61B 5/00* | (2006.01) | |
| *A61B 5/11* | (2006.01) | |
| *A61B 7/02* | (2006.01) | |

(52) U.S. Cl.
CPC ............ *A61B 5/024* (2013.01); *A61B 5/1118* (2013.01); *A61B 5/686* (2013.01); *A61B 5/7275* (2013.01); *A61B 7/02* (2013.01); *A61B 2562/0219* (2013.01)

(58) Field of Classification Search
CPC ...................................................... A61B 5/024
See application file for complete search history.

(56) References Cited

U.S. PATENT DOCUMENTS

| | | | |
|---|---|---|---|
| 7,819,814 | B2 | 10/2010 | Gavriely et al. |
| 8,027,726 | B2 | 9/2011 | Ternes |
| 8,597,197 | B2 | 12/2013 | Patangay et al. |
| 2005/0102001 | A1 | 5/2005 | Maile et al. |
| 2006/0270939 | A1 | 11/2006 | Wariar et al. |
| 2006/0282000 | A1 | 12/2006 | Zhang et al. |
| 2007/0010751 | A1 | 1/2007 | Amano et al. |

(Continued)

FOREIGN PATENT DOCUMENTS

WO    WO-2007011565 A1    1/2007

OTHER PUBLICATIONS

"U.S. Appl. No. 14/195,626, Final Office Action dated Nov. 3, 2015", 6 pgs.

(Continued)

*Primary Examiner* — Carl H Layno
*Assistant Examiner* — Jennifer L Ghand
(74) *Attorney, Agent, or Firm* — Schwegman Lundberg & Woessner, P.A.

(57) ABSTRACT

An apparatus, such as a cardiac function management system can detect heart sounds following a sensed transition in physical activity level, such as from an elevated physical activity level to rest. A technique can include systems, methods, machine-readable media, or other techniques that can include identifying a physical activity level transition, receiving a heart sound signal, determining characteristics of the heart sound and subject physiologic activity to provide an indication, such as a heart failure status indication.

18 Claims, 3 Drawing Sheets

(56) References Cited

U.S. PATENT DOCUMENTS

| | | |
|---|---|---|
| 2007/0021678 A1 | 1/2007 | Beck et al. |
| 2008/0188763 A1 | 8/2008 | John et al. |
| 2008/0294214 A1 | 11/2008 | Holmstrom et al. |
| 2011/0106201 A1 | 5/2011 | Bhunia |
| 2011/0201943 A1 | 8/2011 | Beck et al. |
| 2014/0276163 A1 | 9/2014 | Thakur et al. |

OTHER PUBLICATIONS

"U.S. Appl. No. 14/195,626, Non Final Office Action dated Mar. 30, 2015", 7 pgs.

"U.S. Appl. No. 14/195,626, Notice of Allowance dated Jan. 21, 2016", 8 pgs.

"U.S. Appl. No. 14/195,626, Response filed Jan. 13, 2015 to Restriction Requirement dated Nov. 20, 2014", 8 pgs.

"U.S. Appl. No. 14/195,626, Response filed Dec. 30, 2015 to Final Office Action dated Nov. 3, 2015", 9 pgs.

"U.S. Appl. No. 14/195,626, Restriction Requirement dated Nov. 20, 2014", 6 pgs.

"U.S. Appl. No. 14/195,626, Response filed Jun. 30, 2015 to Non Final Office Action dated Mar. 30, 2015", 12 pgs.

DIAGNOSTIC AND OPTIMIZATION USING EXERCISE RECOVERY DATA

CLAIM OF PRIORITY

This application is a continuation of U.S. Application Ser. No. 14/195,626, filed Mar. 3, 2014, now U.S. Pat. No. 9,345,410, which claims the benefit of priority under 35 U.S.C. § 119(e) of U.S. Provisional Patent Application Ser. No. 61/798,452, filed on Mar. 15, 2013, which is herein incorporated by reference in its entirety.

BACKGROUND

Congestive heart failure (CHF) can be characterized as an inability for the heart to provide sufficient oxygenated blood to meet metabolic demand. For example, weak myocardial tissue can impair heart function, such as resulting in a diminished capacity to pump and circulate blood into pulmonary or systemic circulation. CHF can be accompanied by circulatory impairment resulting in a failure to deliver adequate blood and oxygen supply to peripheral tissues, including vital organs. CHF can become progressively more severe and, if left untreated, can be fatal.

Beck et al., U.S. Patent Application No. 2011/0201943, titled "KINETICS OF PHYSIOLOGIC RESPONSE TO ACTIVITY DURING ACTIVITIES OF DAILY LIVING," refers to using a physiologic response to activity during activity to generate useful diagnostic information about a subject. Beck et al., U.S. Patent Application No. WO/2007/011565, titled "MONITORING PHYSIOLOGIC RESPONSES TO STEADY STATE ACTIVITY," refers to systems and methods for monitoring physiologic responses to a steady state activity.

Overview

Patients with CHF can exhibit impaired cardiovascular recovery after physical activity as compared to healthy adults. For example, CHF patients may exhibit markedly reduced cardiac output paired with excessive hyperventilation secondary to exercise. CHF-related physiologic responses such as heart rate, stroke volume, or respiratory activity can return to baseline levels at a slower rate after exercise than comparable recovery rates for healthy individuals. CHF patients can also abruptly decompensate, requiring hospitalization. Accordingly, CHF patients can benefit from monitoring of a physiologic response to activity, such as to detect or predict such decompensation.

In various examples, cardiac rhythm or function management devices can include one or more sensors to monitor physiologic activity. Some cardiac rhythm or function management devices can be configured to sense changes in physiologic indices, thus providing an indication of heart failure status. In an example, an implantable medical device, such as a monitoring device or cardiac function management device, can receive physiologic data, and log various physiologic parameters at steady states of multiple activity levels.

In one approach, a mechanical sensor such as an accelerometer can be used both for monitoring an activity level of a subject, and for obtaining information indicative of heart sounds. Such dual-use of a mechanical sensor may confound logging of heart sound parameters at multiple activity levels because mechanical or acoustic acceleration information associated with an increased activity level may mask heart sound detection or may degrade a signal-to-noise ratio of such heart sound detection. Generally, heart sound data might therefore be detected only during specified intervals, such as when a physiologic activity level is low.

This document describes, among other things, systems, methods, machine-readable media, or other techniques that can include a sensor configured to sense both physical activity of a subject and an acoustic physiologic heart sound of the subject and provide a resulting sensor signal, and a signal processing circuit to receive the sensor signal, detect a physical activity level transition and a corresponding heart sound characteristic, and determine a resulting physiologic indicator using the heart sound characteristic.

Because recovery from exercise takes a finite amount of time (e.g., recovery is not instantaneous), heart sounds measured at rest or at lower activity almost immediately following elevated activity may be classified as having occurred during the elevated activity, for purposes of physiologic status monitoring. For example, the techniques described herein can include detecting a physical activity level transition and classifying a heart sound characteristic as being associated with a corresponding pre-transition physical activity level to provide an indication, such as a heart failure status indication. The techniques can include detecting multiple physical activity level transitions from an initial elevated physical activity level activity to an initial lowered physical activity level, and a subsequent elevated physical activity level to a subsequent lowered physical activity level. An initial heart sound signal can be detected in response to the initial physical activity level transition and a subsequent heart sound signal can be detected in response to the subsequent physical activity level transition. Determinations of initial and subsequent characteristics about the obtained heart sound can be classified as being associated with corresponding pre-transition activity levels to provide an indication, such as a heart failure status indication.

The techniques can include detecting multiple physical activity level transitions from an initial elevated physical activity level to multiple lowered physical activity levels, over time. An initial heart sound signal can be detected at an initial time and a subsequent heart sound signal can be detected at multiple subsequent times. Determinations of initial elevated heart sound characteristics and subsequent multiple lowered heart sound characteristics can be classified as being associated with corresponding pre-transition activity levels to provide an indication, such as a heart failure status indication. Also, a sample interval used for obtaining information from the mechanical sensor can be adjusted, such as using a more coarse sampling interval during periods of relatively higher activity, and a finer (e.g., shorter duration between samples) during periods of relatively lower activity.

The present inventors have recognized, among other things, that a problem to be solved can include providing a surrogate for heart sound parameters as a function of activity. The present subject matter can provide a solution to the noted problem, such as by determining one or more heart sound characteristics following physical activity levels to provide an indication, such as heart failure status indication. The present subject matter can also provide a potential advantageous alternative to dobutamine stress test evaluation.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An apparatus, such as an implantable monitor, an external monitor, or a cardiac function management system can detect heart sounds following a transition in physical activity level, such as from an elevated physical activity level to a lower physical activity level, such as rest. A cardiac function management system can determine one or more heart sound characteristics concomitant with a transition in physical activity level. A cardiac function management system can classify as being associated with one or more heart sound characteristics to a corresponding pre-transition physical activity level, to provide a heart sound surrogate. The cardiac function management system can log data regarding the heart sound surrogate and can provide an indication, such as a heart failure status indication.

Figure 1:
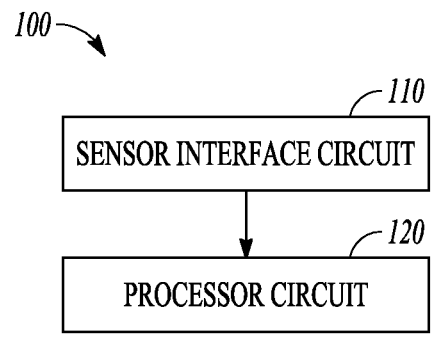
FIG. 1 illustrates generally an example of a system including a sensor interface circuit, and a signal processing circuit.

FIG. 1 illustrates generally an example of a system 100 that can include a sensor interface circuit 110 and a processor circuit 120. The sensor interface circuit 110 can include an implantable or external sensor that can be configured to sense both (1) physical activity of a subject and (2) an acoustic physiologic heart sound of the subject. The sensor interface circuit 110 can obtain at least one sensor signal.

The sensor interface circuit 110 can be configured to receive an indication of physical activity of a subject, such as an electrical signal representative of physical activity, such as from an accelerometer. The sensor interface circuit 110 can be configured to receive the physical activity signal from a single or multiple axis accelerometer, such as to sense an acceleration of the subject indicative of physical activity. The sensor interface circuit 110 can be configured to process the physical activity signal and provide a resulting physical activity indication. The physical activity signal can be indicative of a physical activity level of a subject. The sensor interface circuit 110 can be used for other purposes, such as to sense the subject's posture, heart sounds, or any other information available from a physical activity sensing device, such as an accelerometer.

The sensor interface circuit 110 can be configured to receive an indication of an acoustic physiologic heart sound of the subject, such as an electrical signal representative of an acoustic physiologic heart sound, such as by an implantable or external sensor. The acoustic physiologic heart signal provided by the acoustic sensor can include an indication of energy of at least one heart sound, such as, a S1, S2, S3, S4 heart sound, or any component thereof. The acoustic physiologic heart signal can be used to provide a heart timing interval. The sensor interface circuit 110 can include a respiration sensor, such as an impedance or other sensor, which can include electrodes that can be configured to deliver a test energy, such as to the subject's thorax, and to sense a responsive voltage signal, such as a signal indicative of the thoracic impedance, and which can be filtered to provide information about respiration, heart contraction, or thoracic fluid accumulation.

The signal processing circuit 120 can be coupled to the sensor interface circuit to receive the at least one sensor signal. The signal processing circuit 120 can be configured to detect a physical activity level transition and a corresponding heart sound characteristic. The signal processing circuit 120 can determine a resulting physiologic indicator using the heart sound characteristic. The heart sound characteristic can be classified as being associated with the physical activity level, such as an elevated physical activity level, to provide a surrogate of a heart sound at an elevated physical activity level. The signal processing circuit 120 can determine a physiologic indication using the physical activity level transition and heart sound characteristic information.

The signal processing circuit 120 can be configured to detect a more than one physical activity level transition, such as a first and second physical activity level transition, and more than one corresponding heart sound characteristic, such as a first and second corresponding heart sound characteristic. The first and second heart sound characteristic can be classified as being associated with the first and second physical activity level, such as a first elevated physical activity level and a second elevated physical activity level, lower than the first, to provide a surrogate of a heart sound at an elevated physical activity level. The signal processing circuit 120 can determine a resulting first and second physiologic indication using the first and second physical activity level transition and first and second heart sound characteristic information.

The at least first and second characteristics of the heart sound signal can be of the same type, for example, the first characteristic can include heart sound amplitude following a first physical activity level transition and the second characteristic can include heart sound amplitude following a second physical activity level transition.

Information from the determined physiologic indication can be used to provide a heart failure indication. The physiologic indication can be used to modify pacing or resynchronization therapy, such as using the systems and methods described herein.

The signal processing circuit 120 can be configured to report (or make available) one or more physiologic indications to an external module (e.g., to an external programmer, to a clinician's handheld mobile device, to a user's email, etc.). The signal processing circuit 120 can be configured to provide a cardiac stimulation indication for a plurality of cardiac cycles, to count or store one or more of the results from the determined physiologic indication such as can be counted or stored in a histogram, and, when a heart failure indication is provided, the processor can be configured to do one or more of the following:

(1) provide an alert to an external module;
(2) reduce the stimulation energy to save power;
(3) increase the stimulation energy;
(4) switch to a different pacing configuration (e.g., different pacing waveform, site, etc.); or
(5) initiate a test to determine the interval over a set period of time. The obtained indications can be trended and information about the trending can be provided to an external module and can be displayed to the user.

The signal processing circuit 120 can be configured to increase stimulation energy (e.g., stimulation energy must be provided to exceed the pacing threshold so as to elicit a heart contraction) in response to a heart failure indication. The stimulation energy can be increased after a time period (e.g., a number of hours, days, etc.), after a number of cardiac cycles, or after a number of determined physiologic indications, among other things.

In an illustrative example, such as in response to a heart failure indication, one or more pacing parameters related to a cardiac resynchronization therapy (CRT) can be modified. Such parameters can include one or more of an interventricular (V-V) pacing interval, an atrioventricular delay (AVD), a pacing amplitude, a pacing pulse width, a lead or electrode configuration used for pacing, or one or more other parameters. For example, CRT therapy can be initiated or modified in response to a worsening heart failure status indication, or CRT therapy can be inhibited or modified in response to an improving heart failure status indication.

Figure 2:
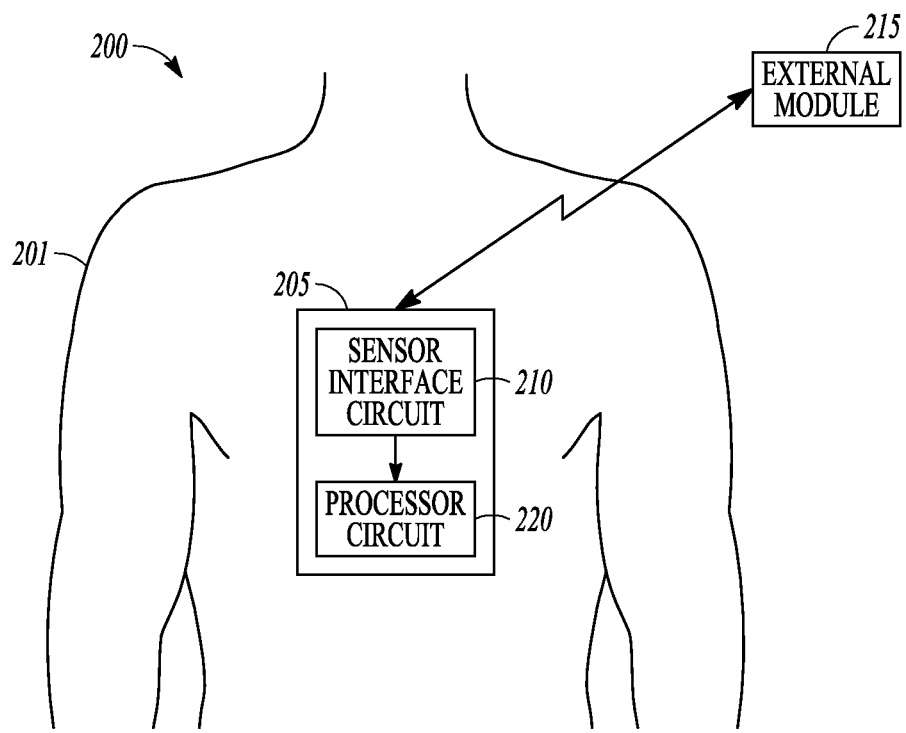
FIG. 2 illustrates generally an example of a system including an implantable medical device (IMD) in a subject, the IMD wirelessly coupled to an external module.

FIG. 2 illustrates generally an example of a system 200 including an ambulatory or implantable medical device (IMD) 205 in a subject 201, the IMD 205 wirelessly coupled to an external module 215. In an example, the IMD 205 can include the sensor interface circuit 210 and the processor circuit 220. In certain examples, a portion of the functionality of one or more of the sensor interface circuit 210, or the processor circuit 220 can occur in the IMD 205, and another portion elsewhere (e.g., in an external component, such as a 12-lead ECG).

In an example, the IMD 205 can include a pacemaker, a defibrillator, or one or more other implantable medical devices. In an example, the IMD 205 can include an antenna configured to provide radio-frequency or other communication between the IMD 205 and the external module 215, or other external device. In an example, the external module 115 can include an antenna. In an example, the external module 215 can include a local medical device programmer or other local external module, such as within wireless communication range of the IMD 205 antenna. The external module 215 can include a remote medical device programmer or one or more other remote external modules (e.g., outside of wireless communication range of the IMD 205 antenna, but coupled to the IMD 205 using a local external device, such as a repeater or network access point). In an example, the external module 215 can be configured to send information to or receive information from the IMD 205. The information can include medical device programming information, subject data, device data, or other instructions, alerts, or other information. In an example, the external module 215 can be configured to display information (e.g., received information) to a user. Further, the local programmer or the remote programmer can be configured to communicate the sent or received information to a user or physician, such as by sending an alert via email of the status of the subject 201 or the system 200 components.

Figure 3:
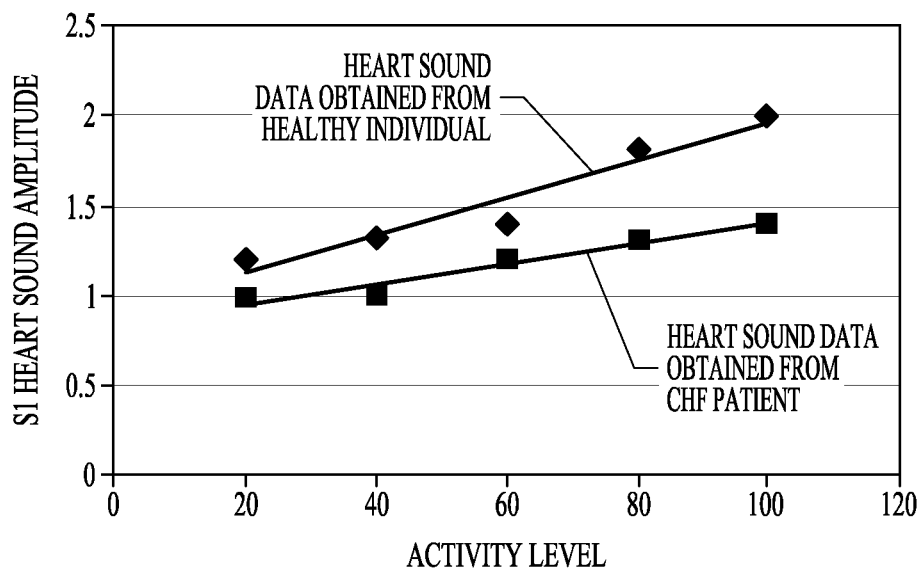
FIG. 3 illustrates generally a conceptual example demonstrating heart sound amplitude classified as being associated with an elevated physical activity level.

FIG. 3 illustrates a conceptual example demonstrating a plot of heart sound S1 amplitude obtained after a physical activity level transition and classified as being associated with the corresponding elevated physical activity level. A heart sound can be obtained at a first time when a patient's physical movement does not confound the heart sound, such as when the accelerometer indicates a physical activity level of about 0 mG or less than a threshold value, such as about 5 mG. In an example, a heart sound can be obtained when a patient reaches a resting state, or at any point at which the physical activity level of the patient is low enough that a meaningful heart sound can be obtained. The first time point at which the physical activity level of the patient is low enough to permit obtaining a meaningful heart sound can be referred to as $t_0$. In an example, a heart sound obtained at $t_0$ can be obtained at substantially similar physical activity levels. For example, a transition from an elevated physical activity level to $t_o$ can be occur when a patient transitions to rest, or when a patient transitions to near rest, such as when a patient transitions from running to walking.

An indication of a transition from an elevated physical activity level to a lower physical activity can be obtained, such as by an accelerometer. The obtained heart sound can be classified as being associated with the pre-transition physical activity level, such as the elevated physical activity level. Because cardiac recovery from an elevated activity level is not instantaneous, a heart sound obtained at the first time immediately following a transition to a lower activity level, such as rest, can reflect cardiac function at the pre-transition elevated physical activity level. The reflected cardiac function at the pre-transition elevated level can provide a surrogate for a heart sound obtained during that particular elevated level of physical activity. For example, a heart sound can be obtained at to after an activity level of 20 mG can be characterized as a heart sound reflective of cardiac function at 20 mG. In an example, information about the cardiac function from a single transition can provide a heart failure status indication.

In the example of FIG. 3, a heart sound obtained after a first elevated activity level transition and classified as being associated with the pre-transition elevated physical activity level is plotted on a graph. A heart sound obtained after a second elevated activity level transition can also be plotted on a graph. A heart sound obtained after a third, fourth, fifth, or more than a fifth elevated activity level transition can also be plotted on a graph. A trend line can be applied to the plots. The slope of the trend line can provide a heart failure status indication.

In the example of FIG. 3, a first trend line is applied to heart sound data obtained from a CHF patient. In the example of FIG. 3, a second trend line is applied to heart sound data obtained from an asymptote. An intercept of heart sound data obtained from a CHF patient can be lower than an intercept of heart sound data obtained from an asymptote. The slope of a trend line applied to heart sound data obtained from a CHF patient can be shallow in comparison to the slope of a trend line applied to heart sound data obtained from an asymptote. Thus, for a particular patient, an intercept or slope of a trend line for that patient can be compared to a specified template intercept or slope indicative of asymptomatic sound data, to a specified template intercept or slope indicative of CHF heart sound data, or to both. Using information about the comparison, an indication or alert of heart failure status can be provided, such as when the slope of the particular patient's trend line falls below a specified threshold slope, for example.

In the example of FIG. 3, the heart sound reflective of cardiac function at an elevated physical activity level is S1 amplitude. In an example, S2, S3, S4, amplitude or energy, or any combination thereof can be used.

Figure 4:
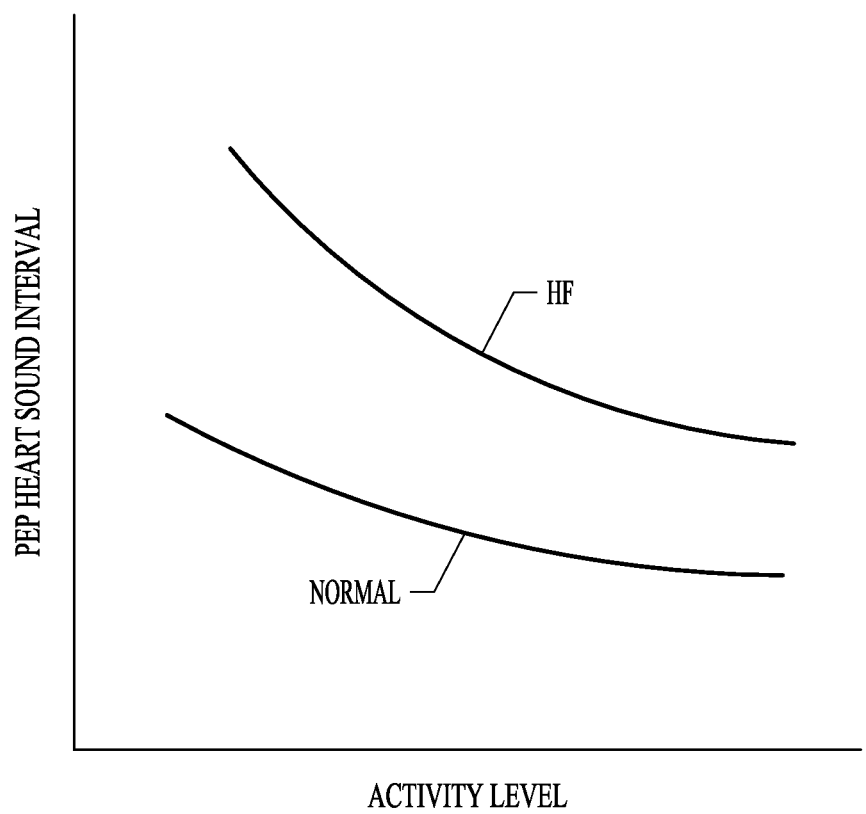
FIG. 4 illustrates generally a conceptual example demonstrating a heart sound timing interval classified as being associated with an elevated physical activity level.

FIG. 4 illustrates a conceptual example demonstrating a plot of multiple heart timing intervals obtained after a physical activity level transition and classified as being associated with a corresponding preceding elevated physical activity level. For example, a heart timing interval can be obtained after a transition from an elevated physical activity level to a lower physical activity level. In an example, a heart timing interval can be obtained at $t_o$. The obtained heart timing interval can be classified as being associated with a pre-transition activity level, such as an elevated physical activity level. For example, a heart timing interval indication can provide a surrogate for heart timing at an elevated physical activity level. In an example, information about a heart timing interval following a single transition can provide a heart failure status indication.

In the example of FIG. 4, a trend line is applied to a heart timing interval data plot obtained from monitoring a CHF patient. In the example of FIG. 3, a trend line is applied to a heart timing interval data plot obtained from monitoring a normal patient. In an example, heart timing interval data can include information about the pre-ejection period (PEP) interval, based on heart sounds. A PEP heart timing interval obtained from a CHF patient can be elongated when compared to a normal PEP heart timing interval. As a CHF patient's activity level increases, the patient's heart rate can increase and the PEP heart timing intervals can shorten. Therefore, the CHF patient's PEP heart timing interval can be compared to a PEP heart timing threshold to provide a heart failure status indication.

In the example of FIG. 4, the heart timing interval reflective of cardiac function at an elevated physical activity level is the PEP interval. Other heart timing interval data, based on heart sounds, can be obtained, such as the Left Ventricular Ejection Time (LVET) interval, for example. In an example, a LVET heart timing interval obtained from a CHF patient can be shortened when compared to a normal LVET heart timing interval. Therefore, the CHF patient's LVET heart timing interval can be compared to a LVET heart timing threshold to provide a heart failure status indication. Any other heart timing intervals can be obtained, such as Q-S1, Q-S2, S1-S2, R-S1, R-S2, S2-S3, S2-R, or S3-R. For example, timing of any of S1, S2, S3, or S4 heart sounds from a fiducial point can be obtained.

In the example of FIG. 4, a first heart timing interval obtained after a first elevated physical activity level transition and classified as being associated with the pre-transition elevated physical activity level is plotted on a graph. A second heart timing interval obtained after a second elevated activity level transition can also be plotted on a graph. Any subsequent heart timing interval obtained following a subsequent elevated activity level transition can also be plotted on a graph. When more than one obtained heart timing interval is plotted on a graph, a trend line can be applied to the first and second plotted data points. The slope of a trend line applied to heart sound data obtained from a CHF patient can be shallow in comparison to the slope of a trend line applied to heart sound data obtained from a healthy patient. Thus, for a particular patient, the slope of a trend line for that patient can be compared to a specified template trend line slope indicative of a healthy slope, to a specified template trend line slope indicative of a CHF slope, or to both. Using information about the comparison, an indication or alert of heart failure status can be provided, such as when the slope of the particular patient's trend line falls below a specified threshold slope, for example.

Figure 5:
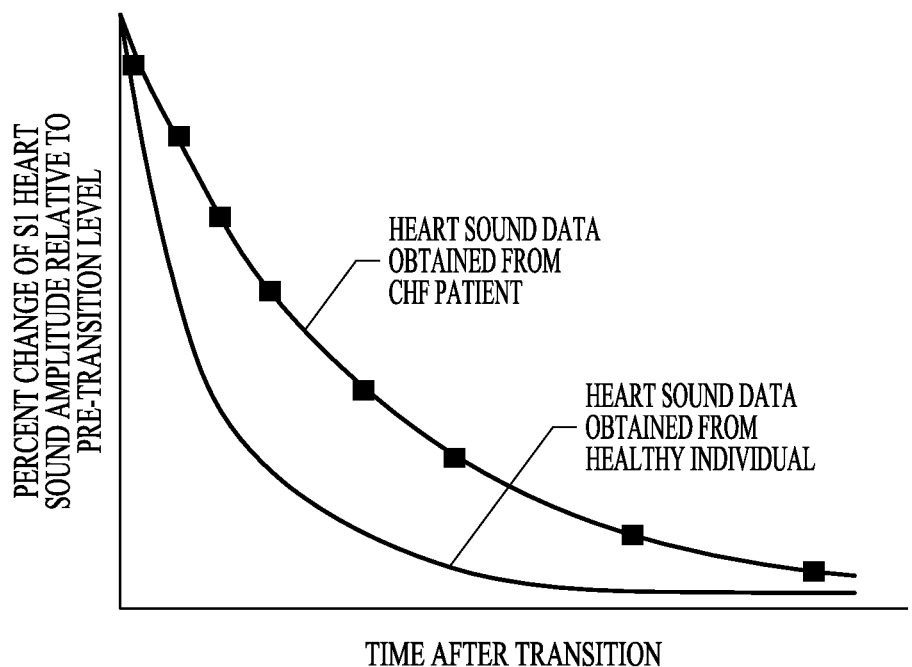
FIG. 5 illustrates generally a conceptual example demonstrating heart sound amplitude following physical activity as a function of time.

FIG. 5 illustrates a conceptual example demonstrating a plot of heart sound amplitude obtained after a physical activity level transition as a function of time. In an example, a heart sound can be obtained at $t_o$, and can be classified as being associated with the pre-transition physical activity level. In an example, multiple heart sounds can be obtained over a period of time. For example, a heart sound can be obtained at $t_0$, 30 sec after $t_0$, 1 min after $t_0$, 1 min 30 sec after $t_0$, 2 min after $t_0$, 2 min 30 sec after $t_0$, 3 min after $t_0$, and 3 min 30 sec after $t_0$ and every 30 sec thereafter until a predetermined threshold has been reached. In an example, a heart sound can be obtained at any repetitive or other specified interval until a specified asymptote or predetermined threshold from a specified asymptote has been reached.

In an example, a first and second heart sound can be taken at a first and second time after an elevated activity level. The percent change can be determined by comparing a first and second heart sound. For example, a first heart sound can be obtained at $t_o$. A second heart sound can be obtained at 30 sec after $t_0$, for example. A second heart sound can be obtained at any time after $t_o$. A third, fourth, fifth or more heart sounds can be obtained at any time after $t_0$. The percent change in heart sound, such as heart sound amplitude, relative to a first heart sound, such as relative to a first heart sound obtained at $t_0$ can be computed.

In an example, a percent change between a heart sound obtained at $t_o$ and a heart sound obtained at a time subsequent to $t_0$, such as, 30 sec after $t_0$, 1 min after $t_0$, 1 min 30 sec after $t_0$, 2 min after $t_0$, 2 min 30 sec after $t_0$, 3 min after $t_0$, and 3 min 30 sec after $t_0$ and every 30 sec thereafter until a predetermined threshold has been reached, can be plotted on a graph. A trend line can be added to the data plot. In an example, when a percent change in heart sound, such as amplitude, is expressed as a function of time, a decaying exponential-like decay curve can be provided.

In the example of FIG. 5, after cessation of physical activity, a healthy heart rate can decrease rapidly. After cessation of physical activity, a CHF heart rate can decrease less rapidly than the healthy heart rate decrease. In an example, the exponential decay curve representative of healthy heart sound amplitude as a function of time can be plotted on the same graph as an exponential decay curve representative of CHF heart sound amplitude as a function of time. An exponential decay curve representative of healthy heart sound amplitude can be compared to an exponential decay curve representative of CHF heart sound amplitude. For example, a CHF heart sound amplitude curve can be compared to a healthy heart sound amplitude curve to compute a characteristic decay time constant of the curve. A CHF heart sound amplitude curve can be compared to a healthy heart sound amplitude curve to compute a correlation between the curves. A decay curve that is shallower than decay curve representative of healthy heart can provide a heart failure indication.

In the example of FIG. 5, the heart sound reflective of cardiac function at an elevated physical activity level is S1 amplitude. In an example, S2, S3, S4, amplitude, or any combination thereof can be obtained and used to provide a heart failure indication as described above.

Figure 6:
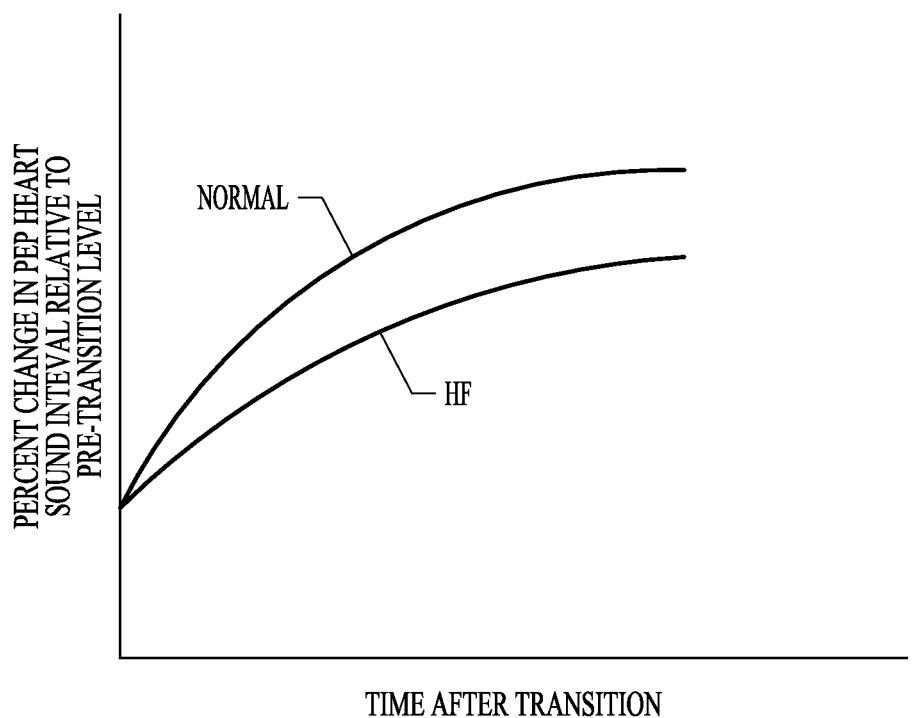
FIG. 6 illustrates generally a conceptual example demonstrating a heart sound timing interval following physical activity as a function of time.

FIG. 6 illustrates a conceptual example demonstrating a plot of heart sound timing interval obtained after an activity level transition as a function of time. For example, a heart sound timing interval can be obtained at $t_0$, and can be classified as being associated with a pre-transition physical activity level, such as the elevated physical activity level. In an example, multiple heart sound timing intervals can be obtained over a period of time at and after $t_0$, such as described above. In an example, a heart sound can be obtained at any repetitive interim until a predetermined threshold has been reached.

In an example, a first and second heart sound timing interval can be taken at a first and second time after an elevated activity level. The percent change can be determined by comparing a first and second heart sound timing intervals obtained at a time after $t_0$, as described above. The percent change in a heart sound timing interval, relative to a first heart sound timing interval, such as relative to a first heart sound timing interval obtained at $t_0$, can be computed.

In an example, a percent change between a heart sound timing interval obtained at $t_0$ and a heart sound obtained at a time subsequent to $t_0$, such as, 30 sec after $t_0$, 1 min after $t_0$, 1 min 30 sec after $t_0$, 2 min after $t_0$, 2 min 30 sec after $t_0$, 3 min after $t_0$, and 3 min 30 sec after $t_0$ and every 30 sec thereafter until a predetermined threshold has been reached, can be plotted on a graph. A trend line can be added to the data plot. In an example, when a percent change in heart timing intervals, such as PEP intervals, is expressed as a function of time, an exponential growth curve can be provided.

In the example of FIG. 6, after cessation of physical activity, a healthy heart rate recovery can include lengthening of a heart timing interval. After cessation of physical activity, a CHF heart timing interval can lengthen less rapidly than a lengthening of a heart timing interval of a healthy heart. In an example, an exponential growth curve representative of a percent change in a healthy heart timing interval after an activity level as a function of time can be plotted on the same graph as an exponential growth curve representative of a percent change in a CHF heart timing interval after an activity level as a function of time. An exponential growth curve representative of percent change of healthy heart timing interval as a function of time can be compared to an exponential growth curve representative of percent change of CHF heart timing interval as a function of time. For example, a CHF heart timing interval curve can be compared to a healthy heart timing interval curve to compute a characteristic growth time constant of the curve. A CHF heart timing interval curve can be compared to a healthy heart timing interval curve to compute a correlation between the curves. A growth curve that is shallower than a growth curve representative of healthy heart can provide a heart failure indication.

Any other heart timing intervals can be obtained, such as Any other heart timing intervals can be obtained, such as Q-S1, Q-S2, S1-S2, R-S1, R-S2, S2-S3, S2-R, or S3-R. For example, timing of any of S1, S2, S3, or S4 heart sounds from a fiducial point can be obtained.

In an example, information about any of the heart failure indications described herein can be used for cardiac monitoring, diagnosing a physiologic condition or disease, treating or providing a therapy for a physiologic condition or disease, or restoring or otherwise altering the function of an organ or a tissue, such as the heart.

ADDITIONAL NOTES & EXAMPLES

The following non-limiting examples can be combined in any permutation or combination.

Example 1 includes subject matter, such as a system, comprising a sensor interface circuit configured to obtain information indicative of both (1) a physical activity of a subject and (2) a heart sound of the subject from the same mechanical sensor, and to provide a resulting sensor signal. Example 1 can optionally include a signal processor circuit, coupled to the sensor interface circuit to receive the sensor signal, the signal processing circuit configured to, using information about the sensor signal, detect a physical activity level transition from an elevated activity level to a less elevated activity level, and identify a heart sound relative to the physical activity level transition. Example 1 can optionally include a signal processor circuit configured to, using information about the sensor signal, determine a heart sound characteristic of the identified heart sound, and determine a resulting physiologic indicator using the determined heart sound characteristic.

In Example 2, the subject matter of Example 1 can optionally include a heart sound characteristic including an indication of an energy of at least one of an S1, S2, S3, or S4 heart sound identified relative to the physical activity level transition.

In Example 3, the subject matter of Example of one or any combination of Examples 1-2 can optionally include a signal processing circuit configured to determine the heart sound characteristic by determining a heart timing interval based on a heart sound identified relative to the physical activity level transition.

In Example 4, the subject matter of one or any combination of Examples 1-3can optionally include a sensor interface circuit configured to obtain information indicative of a first physical activity level transition from a first elevated activity level to a first lower activity level, and a second physical activity level transition from a second elevated activity level to a second lower activity level, and wherein the signal processing circuit is configured to determine a first heart characteristic in response to the first transition and classify the first heart characteristic as being associated with the first physical activity level transition, and determine a second heart characteristic in response to the second transition and classify the second heart characteristic as being associated with the second physical activity level transition.

In Example 5, the subject matter of one or any combination of Examples 1-4can optionally include a signal processing circuit configured to determine a first and second characteristic of the identified heart sound including first and second amplitudes of a first and second heart sound associated with the physical activity level transition.

In Example 6, the subject matter of one or any combination of Examples 1-5can optionally include a signal processing circuit configured to identify a first heart sound and second heart sound, occurring after a first and second activity level transition, and determine respective first and second characteristics of the first and second heart sounds including determining respective first and second heart sound timing intervals, of the same type, defined at least in part by a respective feature of the heart sound.

In Example 7, the subject matter of one or any combination of Examples 1-6can optionally include a signal processing circuit configured to determine a first and second characteristic of heart sound timing interval, in response to the same initial physical activity level transition, and wherein the signal processing circuit is configured to determine the physiologic indication about the subject using the first characteristic with the corresponding first characteristic heart sound timing information, and the second characteristic with the corresponding second heart characteristic heart sound timing information.

In Example 8, the subject matter of one or any combination of Examples 1-7can optionally include a signal processing circuit configured to determine the physiologic indication about the subject using the first characteristic with timing information corresponding to a first instance after the transition; and the second characteristic with timing information corresponding to a subsequent second instance after the transition.

In Example 9, the subject matter of one or any combination of Examples 1-8can optionally include a signal processing circuit configured to determine, as the first and second characteristics of the heart sound signal first and second amplitudes of the heart sound signal, or first and second heart sound timing intervals, of the same type, defined at least in part by a feature of the heart sound signal.

In Example 10, the subject matter of one or any combination of Examples 1-9can optionally include a mechanical sensor.

In Example 11, the subject matter of one or any combination of Examples 1-10can optionally include a mechanical sensor, the sensor interface circuit, and the signal processor circuit are included as respective portions of an implantable medical device, and wherein the mechanical sensor comprises an accelerometer.

In Example 12, the subject matter of one or any combination of Examples 1-11can optionally include subject matter (such as a method, a means for performing acts, or a machine-readable medium including instructions that, when performed by the machine, cause the machine to perform acts) that can include obtaining both (1) a physical activity of a subject and (2) a heart sound of the subject from the same mechanical sensor. Example 12 can optionally include providing a resulting sensor signal. Example 12 can optionally include detecting a physical activity level transition from an elevated activity level to a less elevated activity level using the resulting sensor signal. Example 12 can optionally include identifying a heart sound relative to the physical activity level transition. Example 12 can optionally include determining a heart sound characteristic of the identified heart sound and determining a resulting physiologic indicator using the determined heart sound characteristic.

In Example 13, the subject matter of one or any combination of Examples 1-12can optionally include determining a heart sound characteristic of the identified heart sound including using an indication of energy of at least one of an S1, S2, S3, or S4 heart sound identified relative to the physical activity level transition.

In Example 14, the subject matter of one or any combination of Examples 1-13can optionally include determining a heart sound characteristic of the identified heart sound including determining a heart sound timing interval involving a heart sound identified relative to the physical activity level transition.

In Example 15, the subject matter of one or any combination of Examples 1-14can optionally include obtaining both (1) a physical activity of a subject and (2) a heart sound of the subject from the same mechanical sensor including obtaining information indicative of a first physical activity level transition from a first elevated activity level to a first lower activity level, and a second physical activity level transition from a second elevated activity level to a second lower activity level, determining a first heart characteristic in response to the first transition and classifying the first heart characteristic as being associated with the first physical activity level transition, and determining a second heart characteristic in response to the second transition and classifying the second heart characteristic as being associated with the second physical activity level transition.

In Example 16, the subject matter of one or any combination of Examples 1-15can optionally include determining a heart sound characteristic of the identified heart sound including determining first and second amplitudes of a sound associated with the physical activity level transition.

In Example 17, the subject matter of one or any combination of Examples 1-16can optionally include identifying a heart sound relative to the physical activity level transition including identifying a first heart sound and second heart sound, occurring after a first and second activity level transition, and determining respective first and second characteristics of the first and second heart sounds including determining respective first and second heart sound timing intervals, of the same type, defined at least in part by a respective feature of the heart sound.

In Example 18, the subject matter of one or any combination of Examples 1-17can optionally include determining a heart sound characteristic of the identified heart sound including determining a first and second characteristic of heart sound timing in response to the same physical activity level transition and determining a physiologic indication about the subject using the first characteristic with the corresponding first characteristic timing information and the second characteristic with the corresponding second characteristic timing information.

In Example 19, the subject matter of one or any combination of Examples 1-18can optionally include determining a heart sound characteristic of the identified heart sound including determining a first characteristic with timing information corresponding to a first instance after the transition, and determining a second characteristic with timing information corresponding to a subsequent second instance after the transition.

In Example 20, the subject matter of one or any combination of Examples 1-19can optionally include determining a heart sound characteristic of the identified heart sound including determining, as the first and second amplitudes of the heart sound signal, first and second amplitudes, or first and second timing intervals, of the same type, defined at least in part by a feature of the heart sound signal.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method comprising:
    detecting, using a signal processing circuit, a first physical activity level transition from a first elevated activity level to a less elevated activity level using information about a physical activity level of a subject;
    identifying, using the signal processing circuit, multiple cardiac function characteristics using physiologic information of the subject from a physical activity recovery period following the first physical activity level transition; and
    determining, using the signal processing circuit, a physical activity recovery period physiologic indicator of the subject using the identified multiple cardiac function characteristics from the physical activity recovery period;
    wherein the physical activity recovery period includes multiple cardiac cycles immediately following the detected first physical activity level transition.

2. The method of claim 1,
    wherein the identifying the multiple cardiac function characteristics includes identifying heart sound characteristics from the physical activity recovery period; and
    wherein the determining the physiologic indicator includes using the identified heart sound characteristics.

3. The method of claim 2, wherein the identifying the heart sound characteristics includes determining energy indications for at least one of an S1, S2, S3, or S4 heart sound, and wherein the determining the physiologic indicator includes using the determined energy indications.

4. The method of claim 2, wherein the identifying the heart sound characteristics includes determining, using the signal processing circuit, a change in an S1 heart sound amplitude level during the physical activity recovery period relative to an S1 heart sound amplitude level occurring before the physical activity recovery period, and wherein the determining the physiologic indicator includes using the determined change in the S1 heart sound amplitude level.

5. The method of claim 2, wherein the identifying the heart sound characteristics includes determining, using the signal processing circuit, heart sound timing intervals, and wherein the determining the physiologic indicator includes using the determined intervals.

6. The method of claim 2, wherein the identifying the heart sound characteristics includes determining, using the signal processing circuit, a change in a pre-ejection period (PEP) interval during the physical activity recovery period relative to a PEP interval occurring before the physical activity recovery period, and wherein the determining the physiologic indicator includes using the determined change in the PEP interval.

7. The method of claim 2, further comprising:
    receiving an acceleration signal from an accelerometer, the acceleration signal including a first component that includes the information about the physical activity level of the subject and a second component that includes heart sound information about the subject.

8. The method of claim 2, wherein the identifying the heart sound characteristics includes determining, using the signal processing circuit, first and second amplitudes, or first and second timing intervals, of the same type, defined at least in part by a feature of each of the identified heart sound characteristics during the physical activity recovery period and following the first physical activity level transition.

9. The method of claim 1,
    wherein the identifying the multiple cardiac function characteristics includes identifying thoracic impedance characteristics from the physical activity recovery period; and
    wherein the determining the physiologic indicator includes using the identified impedance characteristics.

10. The method of claim 1, wherein the determining physiologic indicator includes using a trend of the identified multiple cardiac function characteristics, including determining a trend line corresponding to the identified multiple cardiac function characteristics and comparing the determined trend line to a reference trend line, the reference trend line corresponding to physiologic characteristic information from a deemed-healthy subject.

11. The method of claim 1, further comprising computing a decay characteristic of a trend line associated with the identified multiple cardiac function characteristics, and wherein the determining the physiologic indicator includes using the decay characteristic.

12. The method of claim 1, wherein the determining the physiologic indicator includes determining a heart failure indication for the subject.

13. The method of claim 1, further comprising receiving cardiac function characteristic information corresponding to a deemed-healthy subject;
   computing a correlation between the determined physiologic indicator of the subject and the received cardiac function information corresponding to the deemed-healthy subject; and
   providing a health status indication for the subject using the computed correlation.

14. A method comprising:
   identifying, using information from a first sensor, a physical activity level transition of a subject from an elevated activity level to a less elevated activity level;
   receiving, at a signal processing circuit and from the first sensor or from a different second sensor, a heart sound signal of the subject;
   identifying, using the signal processing circuit and the heart sound signal, heart sounds from a physical activity recovery period, the physical activity recovery period including multiple cardiac cycles immediately following the identified physical activity level transition;
   determining, using the signal processing circuit, respective heart sound characteristics for the identified heart sounds; and
   determining, using the signal processing circuit, a heart failure status indication using the determined heart sound characteristics from the physical activity recovery period.

15. A system comprising:
   a sensor interface circuit configured to receive one or more sensor signals from one or more physiologic sensors, the one or more sensor signals including information indicative of a physical activity level of a subject and information indicative of cardiac function characteristics of the subject; and
   a signal processing circuit, coupled to the sensor interface circuit to receive the one or more sensor signals, the signal processing circuit configured to:
      detect a physical activity level transition from a first elevated activity level to a less elevated activity level;
      identify multiple cardiac function characteristics from a physical activity recovery period following the detected physical activity level transition; and
      determine a physical activity recovery period physiologic indicator of the subject using the identified multiple cardiac function characteristics from the physical activity recovery period;
      wherein the physical activity recovery period includes multiple cardiac cycles immediately following the detected physical activity level transition.

16. The system of claim 15, wherein the signal processing circuit is further configured to determine, as the physical activity recovery period physiologic indicator, a heart failure status indicator using the identified multiple cardiac function characteristics.

17. The system of claim 15, wherein the sensor interface circuit is configured to receive, as the information indicative of the cardiac function characteristics of the subject, one or more of heart sound information, thoracic impedance information, or respiration information about the subject.

18. The system of claim 15, wherein the signal processing circuit is further configured to determine the physical activity recovery period physiologic indicator using a trend of the identified multiple cardiac function characteristics from the physical activity recovery period.

* * * * *